US00PP37584P2

(12) United States Plant Patent
Snijder

(10) Patent No.: US PP37,584 P2
(45) Date of Patent: Aug. 18, 2026

(54) ***VERBENA* PLANT NAMED 'VEAZ0069'**

(50) Latin Name: *Verbena hybrida*
Varietal Denomination: VEAZ0069

(71) Applicant: SYNGENTA CROP PROTECTION AG, Basel (CH)

(72) Inventor: Ronald Christiaan Snijder, Enkhuizen (NL)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 19/262,184

(22) Filed: Jul. 8, 2025

(51) Int. Cl.
*A01H 5/02* (2018.01)
*A01H 6/86* (2018.01)

(52) U.S. Cl.
USPC ..... Plt./308
CPC ..... *A01H 6/86* (2018.05)

(58) Field of Classification Search
USPC ..... Plt./308
CPC ..... A01H 5/02
See application file for complete search history.

(56) References Cited

PUBLICATIONS https://online.flippingbook.com/view/90219826/120-121/; 2025; 3 pages.*

* cited by examiner

*Primary Examiner* — Kent L Bell
(74) *Attorney, Agent, or Firm* — Dale Skalla

(57) ABSTRACT

'VEAZ0069' is a product of a planned breeding program. The new cultivar has large sized inflorescences, purple-violet florets of large size, medium green toothed leaves, and a plant habit that is initially upright, then outwardly spreading.

1 Drawing Sheet

Latin name of the genus and species of the plant claimed: *Verbena hybrida.*

Varietal denomination: 'VEAZ0069'.

BACKGROUND OF THE NEW PLANT

The present invention comprises a new *Verbena*, botanically known as *Verbena hybrida*, and hereinafter referred to by the variety name 'VEAZ0069'.

'VEAZ0069' is a product of a planned breeding program. The new cultivar has large sized inflorescences, purple-violet florets of large size, medium green toothed leaves, and a plant habit that is initially upright, then outwardly spreading.

'VEAZ0069' originated from a cross made in September 2019 in a greenhouse in Amatitlan, Guatemala.

The female parent was an unpatented proprietary plant 'VERAW2114-59V' having a more vigorous habit and more purple flower color. The male parent was an unpatented proprietary plant designated 'Lanai compact violet with eye', with smaller plant habit and bicolored florets.

The resulting seed was sown in February 2020 in a greenhouse in Enkhuizen, The Netherlands, and 'VEAZ0069' was selected as one flowering plant within the progeny of the stated cross in May 2020.

The first act of asexual reproduction of 'VEAZ0069' was accomplished when vegetative cuttings were propagated from the initial selection in June 2020 in a greenhouse in Enkhuizen, The Netherlands.

BRIEF SUMMARY OF INVENTION

Horticultural examination of plants grown from cuttings of the plant initiated in the fall of 2020, and continuing thereafter, has demonstrated that the combination of characteristics as herein disclosed for 'VEAZ0069' are firmly fixed and are retained through successive generations of asexual reproduction.

'VEAZ0069' has not been observed under all possible environmental conditions. The phenotype may vary significantly with variations in environment such as temperature, light intensity, and day length.

A Plant Breeder's Rights for this cultivar has not yet been applied for. 'VEAZ0069' has not been made publicly available prior to the effective filing date of this application, notwithstanding any disclosure that may have been made less than one year prior to the effective filing date of this application by the inventor or another who obtained 'VEAZ0069' directly from the inventor.

The following traits have been repeatedly observed and are determined to be basic characteristics of the new variety. The combination of these characteristics distinguishes this *Verbena* as a new and distinct variety.

BRIEF DESCRIPTION OF THE PHOTOGRAPHS

The accompanying photographic drawings show typical flower and foliage characteristics of 'VEAZ0069' with colors being as true as possible with an illustration of this type.

Figure 1:
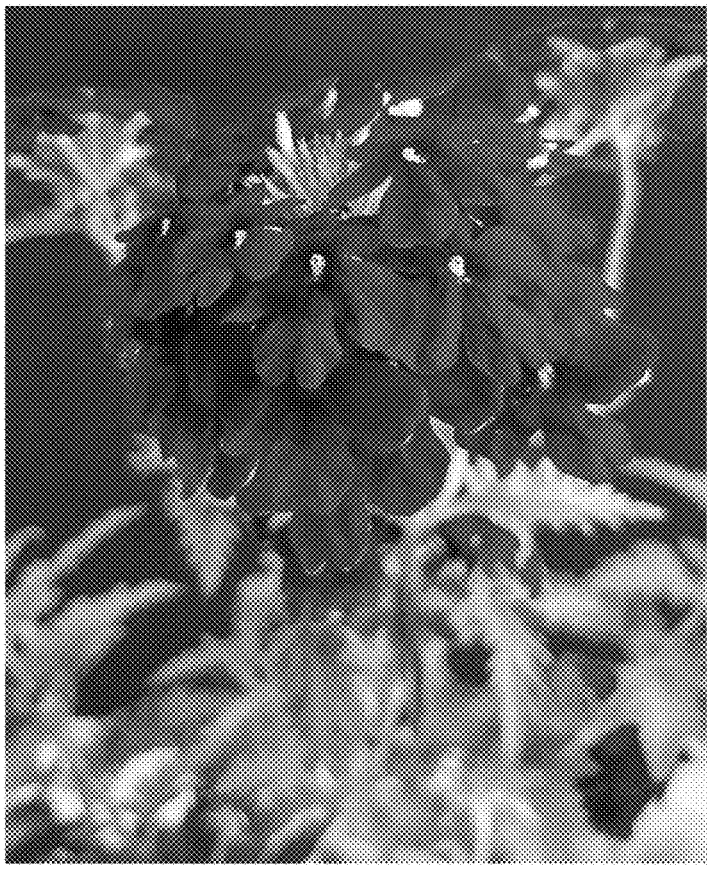
Figure 2:
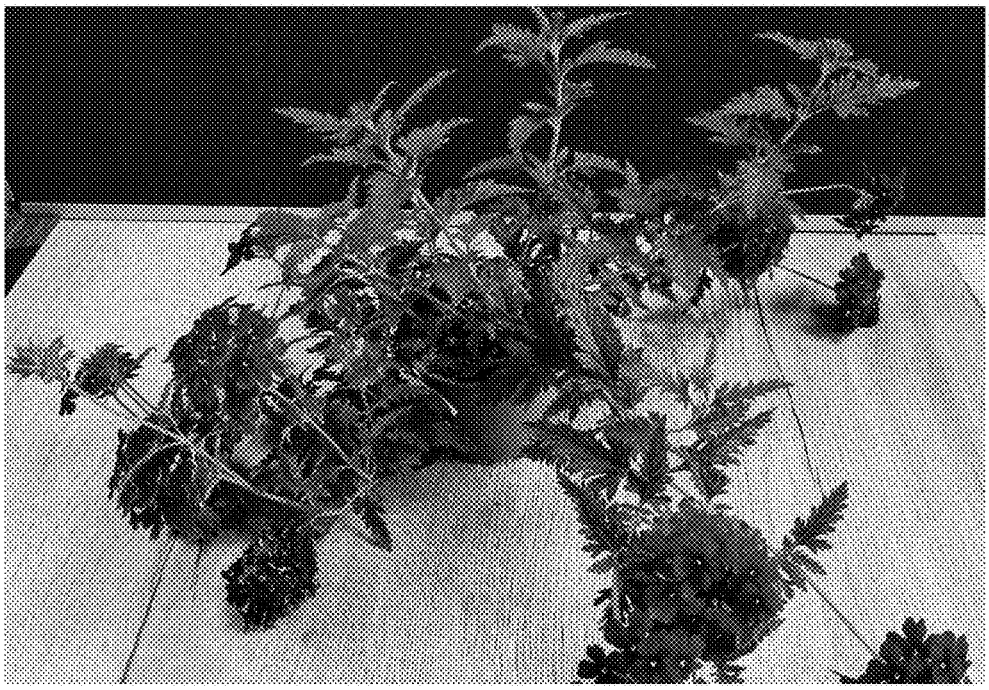

The photographic drawings in FIG. 1 show a close view of an inflorescence of the new plant, and in FIG. 2 a whole flowering plant.

The aforementioned photographs were taken in July 2025 in Andijk, The Netherlands. The plants were about 10 weeks old and were grown in 11 cm pots.

DETAILED BOTANICAL DESCRIPTION

Colour references are made to The Royal Horticultural Society Colour Chart (R.H.S.) 1995.

TABLE 1

DIFFERENCES BETWEEN THE NEW VARIETY 'VEAZ0069' AND A MOST SIMILAR VARIETY

| | 'VEAZ0069' | 'Doveremsucoblu' (described in U.S. Plant Pat. No. 33,464) |
|---|---|---|
| Leaf margin: | Incised | Lobed |
| Upper side of mature petal: | Bluish violet RHS 88A, fading to RHS 88B on the edge | Darker, purplish violet RHS 83A |
| Leaf shape: | Deltoid | Lanceolate |

Plant:

*Form, growth and habit.*—Herbaceous, initially upright, then outwardly spreading; vigorous and free-branching.

*Plant height.*—17 cm.

*Plant height (inflorescence included).*—17 cm.

*Plant width.*—44 cm.

Roots:

*Number of days to initiate and produce roots.*—11-14 days at about 22 degrees C.

*Type.*—Fine, fibrous, free branching.

*Color.*—RHS N155B but whiter.

Foliage:

*Arrangement.*—Opposite, simple.

*Immature, leaf color, upper surface.*—RHS 137A.

*Immature, leaf color, lower surface.*—RHS 139C.

*Mature, leaf color, upper surface.*—RHS 137B.

*Mature, leaf color, lower surface.*—RHS 138B.

*Length.*—5-8 cm.

*Width.*—2-4 cm.

*Shape.*—Deltoid.

*Base shape.*—Attenuate.

*Apex shape.*—Acute.

*Margin.*—Incised.

*Texture, upper surface.*—Hirsute.

*Texture, lower surface.*—Hirsute.

*Color of veins, upper surface.*—Indistinct, RHS 137A.

*Color of veins, lower surface.*—RHS 139C.

*Pattern of veining.*—Pinnate.

*Petiole color.*—RHS 139C.

*Petiole length.*—0-0.1 cm.

*Petiole width.*—0.2-0.3 cm.

*Texture.*—Hirsute.

Stem:

*Branching characteristics.*—Makes branches on every node.

*Quantity of main branches per plant.*—6-12.

*Color of stem.*—RHS 138C.

*Stem length.*—14-25 cm.

*Stem width.*—0.3-0.4 cm.

*Length of internodes.*—2-4 cm.

*Texture.*—Hirsute.

*Colour of peduncle.*—RHS 138B.

*Length of peduncle.*—4-6.5 cm.

*Peduncle diameter.*—0.2 cm.

*Texture.*—Canescent.

Inflorescence:

*Type.*—Umbel-like, but actually a spike, umbrella-shaped, large.

*Blooming habit.*—Flowers continuously through the summer months.

*Lastingness of individual blooms on the plant.*—About 15 days in the greenhouse.

*Number of inflorescences per plant.*—20 at various stages.

*Horizontal diameter of inflorescence.*—About 7 cm.

*Depth of inflorescence.*—5-6 cm.

*Number of florets per inflorescence (including any buds at the time).*—40-55.

Bud: (Just when opening/showing colour).

*Color.*—RHS 87A.

*Length.*—15-17 mm.

*Width.*—0.3 cm.

*Shape.*—Tubular with a bulbous end.

Floret:

*Form.*—Sessile; salver-shape, composed of 5 partly fused petals with a base of a narrow tube.

*Immature color, upper surface.*—Close to RHS 79A at the base, fading to RHS 81A on the edge.

*Immature color, lower surface.*—RHS 82B.

*Mature color, upper surface.*—Close to RHS 88A at the base, fading to RHS 88B on the edge.

*Mature color, lower surface.*—RHS 88D.

*Floret diameter.*—2.7 cm.

*Floret length (depth).*—0.6 cm.

*Number of petals.*—Gamopetalous, 5 lobed.

*Petal length.*—1.2 cm.

*Petal width.*—Upper petal 0.8 cm; lower petal 1.0 cm.

*Shape.*—Obcordate.

*Apex shape.*—Emarginate.

*Margin.*—Entire.

*Petal texture, upper surface.*—Smooth.

*Petal texture, lower surface.*—Papillose.

*Corolla tube length.*—1.9 cm.

*Corolla tube width.*—0.1 cm at base, tapering to 0.3 cm at corolla tube opening.

*Corolla tube color inside.*—157A.

*Tube color outside*—157A.

*Corolla texture, inside.*—Papillose.

*Corolla texture, outside.*—Glabrous.

*Throat hair color.*—RHS 155A.

Calyx:

*Type.*—Five sepals whose margins are fused to each other along their length, with a transparent membrane of less than 0.1 cm in width and with one smaller sepal attached to the base of the calyx.

*Color of upper surface of sepals.*—RHS 138B at apex, RHS 138D at the base.

*Color of the lower surface of sepals.*—RHS 138B at apex, RHS 138D at the base.

*Length of sepals.*—1.7 cm.

*Width of sepals.*—0.15 cm.

*Sepal shape.*—Linear, but fused.

*Apex shape.*—Acute.

*Margins.*—Entire.

*Texture upper surface sepals.*—Densely covered with short hair.

*Texture inner surface sepals.*—Glabrous.

Reproductive organs: Gynoecium.

*Pistil.*—1.

*Pistil length.*—1.8 cm.

*Style color.*—RHS 144D.

*Style length.*—1.7 cm.

*Stigma color.*—RHS 144A.

*Ovary color.*—144B.

*Ovary length.*—0.22 cm.

*Ovary width.*—0.1 cm.

*Androecium stamens.*—Anthers and filaments fused to upper half of corolla tube; four anthers with two pollen sacs per anther.

*Color of filaments.*—RHS 157C.

*Filament length.*—0.15 cm.

*Anther color.*—RHS 151C.

*Anther length.*—0.05 cm.

*Pollen color.*—RHS 1B.

*Pollen amount.*—Scarce.

Fertility/seed set: Neither seed nor fruit production has been observed.

Disease/pest resistance: Resistance to pathogens and pests common to *Verbena* has not been observed.

What is claimed is:

1. A new and distinct variety of *Verbena* plant named 'VEAZ0069' substantially as illustrated and described herein.

* * * * *